US 6,576,674 B2

(12) United States Patent
Cutler et al.

(10) Patent No.: US 6,576,674 B2
(45) Date of Patent: Jun. 10, 2003

(54) METHOD OF CONTROLLING ZOOLOGICAL AND AQUATIC PLANT GROWTH

(75) Inventors: Stephen J. Cutler, Roswell, GA (US); Horace G. Cutler, Watkinsville, GA (US); David Wright, Solomons, MD (US); Rodger Dawson, Owings, MD (US)

(73) Assignee: Garnett, Inc., Watkinsville, GA (US)

( * ) Notice: Subject to any disclaimer, the term of this patent is extended or adjusted under 35 U.S.C. 154(b) by 10 days.

(21) Appl. No.: 10/003,464

(22) Filed: Dec. 6, 2001

(65) Prior Publication Data

US 2002/0098978 A1 Jul. 25, 2002

Related U.S. Application Data

(63) Continuation-in-part of application No. PCT/US01/05117, filed on Feb. 16, 2001, which is a continuation of application No. 09/506,017, filed on Feb. 17, 2000, now Pat. No. 6,340,468.
(60) Provisional application No. 60/237,401, filed on Oct. 4, 2000.

(51) Int. Cl.$^7$ ............... A01N 35/00; A01N 37/00; A61K 31/12; A61K 31/185; A61K 31/19
(52) U.S. Cl. ............... 514/680; 514/553; 514/557; 514/569; 514/577
(58) Field of Search ............... 514/553, 557, 514/569, 577, 680

(56) References Cited

U.S. PATENT DOCUMENTS

| | | |
|---|---|---|
| 2,999,810 A | 9/1961 | Sundholm |
| 3,947,594 A | 3/1976 | Randall |
| 4,465,795 A | 8/1984 | Sunano et al. |
| 5,128,050 A | 7/1992 | Gill |
| 5,154,747 A | 10/1992 | Yokoi et al. |
| 5,192,451 A | 3/1993 | Gill |
| 5,334,386 A | 8/1994 | Lee et al. |
| 5,851,408 A | 12/1998 | Sedivy |
| 5,976,229 A | 11/1999 | Ohmura et al. |
| 6,164,244 A | 12/2000 | Cutler et al. |
| 6,340,468 B1 | 1/2002 | Cutler et al. |

FOREIGN PATENT DOCUMENTS

| | | |
|---|---|---|
| JP | 1031702 | 2/1989 |
| WO | WO0056140 | 9/2000 |

*Primary Examiner*—Alton Pryor
(74) *Attorney, Agent, or Firm*—Roylance, Abrams, Berdo & Goodman, LLP

(57) ABSTRACT

A method of controlling target aquatic microorganism pest populations by exposing the target population to a toxic amount of an aquacidal compound comprising an anthraquinone. The method is particularly effective for treating ballast water of ships or other enclosed volumes of water subject to transport between or among geographic areas to control the relocation of plants, toxic bacteria, and animals contained in the water.

30 Claims, No Drawings

METHOD OF CONTROLLING ZOOLOGICAL AND AQUATIC PLANT GROWTH

This application is a continuation-in-part on PCT application PCT/US01/05117 filed Feb. 16, 2001,which is a continuation of copending U.S. patent application Ser. No. 09/506,017 that was filed on Feb. 17, 2000 now U.S. Pat. No. 6,340,468, and which claim benefit to U.S. rovisional patent application Ser. No. 60/237,401 that was filed on Oct. 4, 2000. The disclosures of these applications are incorporated herein by reference.

FIELD OF INVENTION

The present invention is directed to a method and compositions for controlling aquatic pests, including zoological organisms and plants. More specifically, the invention is directed to a method and composition for controlling, inhibiting, and terminating populations of aquatic and marine pest plants, organisms, and animals in a target treatment zone. The invention is particularly applicable for sterilizing a treated water volume (whether or not enclosed) of mollusks, dinoflagellates, bacteria and algae.

BACKGROUND OF THE INVENTION

The discovery in the Summer of 1988 of the Eurasian zebra mussel *Dressiness polymorph* in the Great Lakes of North America represents one of the most significant events in the history of aquatic biological invasion. However, this was not the first event of a non-indigenous species entering into U.S. water. Earlier, the spiny water flea *Bythotrephes cedarstroemi* and the ruffe *Gymnocephalus cernuus* had entered the United States from ballast water of European ports. It was soon discovered that zebra mussel had also entered the U.S. via ballast water of European origin.

Since the summer of 1988, there have been a number of aquatic species that have entered into the U.S. via ballast water taken from ports of other countries. It is estimated that several hundred organisms have been introduced into the U.S. via ballast water and/or other mechanisms, not limited to fisheries and ocean or coastal currents. As such, the integrity of the coastal waters of the United States and the Great Lakes basin has been substantially threatened by the increased rate of aquatic species introduction from other countries.

Prior to 1880, various methods for controlling ballast in ships were used. In fact, many streets in coastal towns are paved with stones once used for ship ballast. However, shortly before the turn of the century, water as ballast soon replaced these older methods of stabilizing ships. The rate of invasions by non-indigenous aquatic species rose dramatically since the turn of the century, with much of this being attributed to shipping. As transoceanic travel increased, so to has the inadvertent introduction of non-indigenous species that threaten natural waterways. This is a result of the diverse array of organisms that are able to survive the transoceanic travel in ship ballast water, sea chests, and on ship hulls. Of these, the ballast water of ships is one of the primary mechanisms by which organisms have invaded U.S. waters.

Ballast water consists of either fresh or salt water that is pumped into a vessel to help control its maneuverability as well as trim, stability, and buoyancy. The water used for ballast may be taken at various points during the voyage including the port of departure or destination. Container ships may make as many as 12 port visits/ballast exchanges during a single round-the-world journey. Any planktonic species or larvae that is near the ballast intake may be taken up and transported to the next port of destination. Globally, an estimated 10 billion tons of ballast water are transferred each year. Each ship may carry from a few hundred gallons (about 2 metric tons) to greater than 100,000 metric tons depending on the size and purpose. More than 640 tons of ballast water arrive in the coastal waters of the United States every hour.

The risk of invasion through ballast water has risen dramatically in the past 20 years as a result of larger vessels being used to transport greater amounts of material into and out of the U.S. It is estimated that between 3000–10,000 species of plants and animals are transported daily around the world. In regard to those materials being brought into the U.S., it is of interest to note that materials which contain animals, fruits, vegetables, etc., must be inspected by the U.S. Department of Agriculture in order to satisfy requirements that potentially harmful non-indigenous species are excluded. The irony is that the ship may be able to release ballast water that has been contaminated with a non-indigenous species. It is through this mechanism that several hundred species have been introduced into the United States.

The U.S. Fish and Wildlife Service currently estimates that the annual cost to the North American economy due to the introduction of non-indigenous species is more than $100 billion. While ballast water only accounts for a minor proportion of these introductions, the cost still runs to tens of billions of dollars in terms of industrial dislocation, clean-up, loss of product and loss of fisheries and other natural resources.

As noted above, one of the most notorious species introduced in the Great Lakes of North America is the Eurasian zebra mussel *Dreissena polymorpha*, which has become a major threat to inland water supplies from both a recreational and commercial aspect. Unfortunately, their range now extends from the Great Lakes to Louisiana and estimated economic losses are estimated at more than $4 billion for the calendar year 1999. This species is particularly prolific and a reproducing female can expel more than 40,000 fertile eggs per season which, upon hatching, may be found in colonies in excess of one hundred thousand per square meter. Furthermore, the colonies attach themselves to underwater structures that include, amongst others, water intake pipes, from which they can be readily disseminated into other environments, ship hulls, debris such as discarded automobile tires, sunken ships, and discarded metal drums. Established colonies often reach a thickness of 20 cm.

Of particular importance is the clogging of water intake pipes by zebra mussels that have a devastating industrial effect, especially in such uses as power plants, where there is a specific need for reliable water flow rates. Certain power plants have recorded a 50% water flow rate reduction following infestation and, in addition, zebra mussels appear to secrete substances, both in the living and dead state, that cause ferrous metal pipes to degrade. An associated problem also occurs in pipes that supply potable water because even following purification treatment, the water has an off flavor. This is attributed not only to the substances released by the living mussels, but especially by those that have died and are decaying. The latter most probably produce polyamines, such as cadaverine, which has a particularly obnoxious odor associated with decaying proteins and is most often noted in decaying meat.

Other detrimental environmental effects are the result of zebra mussel infestations both directly and indirectly. Of a direct nature are the effects on phytoplankton. Zebra mussels feed on phytoplankton, which are a source of food for fish, especially in lakes and ponds, thereby increasing the photosynthetic efficiency for other aquatic weed species because of increased clarity of the water. This has been shown to have dramatic effects on energy flow and food chains in some waters. Some fish species are threatened. The walleye, for example, thrives in cloudy water and it is generally believed by environmentalists that, increased water clarity resulted from zebra mussel activity will lead to the demise of that industry, presently estimated to be $900 million per year. Large-scale, multi-billion dollar degradations in native Great Lakes fisheries are already being felt as a result of competition from non-fishable species such as the Eurasian ruffe (*Gymnocephalus cernuus*) and the round goby (*Proterorhinus marmoratus*), which have been introduced through ballast water in the last two decades.

As a result of its feeding preferences, zebra mussels may radically alter the species composition of the algal community such that potentially harmful species may become abundant. An example is Microcystis, a blue-green alga of little nutritive value and capable of producing toxins which can cause gastrointestinal problems in humans. There are records of Microcystis blooms in Lake Erie and adjacent waterways. Toxic dinoflagellates such as Prorocentrum, Gymnodinium, Alexandrium and Gonyaulax often appear as blooms, sometimes known as "red tides", in many parts of the world. Apart from causing serious (sometimes fatal) ailments in several vertebrate consumers, including humans, several of these organisms have had devastating effects on shellfish industries in several countries and it is now accepted that ballast-water introductions were responsible in many of these cases.

Reports of the introduction of the cholera bacterium, *Vibrio cholera*, to the Gulf coast of the United States have now been traced to the importation of this species associated with planktonic copepod (crustacean) vectors in ballast water arriving at Gulf coast ports from South America. This, in turn, had been transported from Europe to South American ports by similar means.

As a result of the introduction of non-indigenous species into the United States, and in order to reduce the possibility of the introduction of other organisms in the future, in 1990 the U.S. Congress passed an act known as Public Law 101–646 "The Nonindigenous Aquatic Nuisance Prevention and Control Act" under the "National Ballast Water Control Program" which it mandates, among other things, studies in the control of the introduction of aquatic pests into the U.S. These control measures may include UV irradiation, filtration, altering water salinity, mechanical agitation, ultrasonic treatment, ozonation, thermal treatment, electrical treatment, oxygen deprivation, and chemical treatment as potential methods to control the introduction of aquatic pests. It is likely that other governments will pass similar legislation in the near future as the scope and costs of aquatic pest contamination become better understood.

Numerous methods and compositions have been proposed to control and inhibit the growth of various marine plants and animals. In particular, a number of compositions have been proposed to treat water and various surfaces having infestation of zebra mussels. Examples of various compositions are disclosed in U.S. Pat. Nos. 5,851,408, 5,160,047, 5,900,157 and 5,851,408. Treatment of various aquatic pests, other than toxic bacteria, is described in WO 00/56140 using juglone or analogs thereof.

These prior compositions and methods, although somewhat effective, have not been able to completely control the introduction of marine plants and animals into waterways. Accordingly there is a continuing need in the industry for the improved control of aquatic pests in the form of plants and animals, preferably aquatic flora, fauna, and other organisms that can be suspended in water and are susceptible to geographic migration by water intake, currents, or tides.

SUMMARY OF THE INVENTION

The present invention is directed to a method of controlling aquatic pests in the form of plants, animals, bacteria, or other microorganisms. The invention is particularly well suited for population control and sterilization of mollusks, dinoflagellates, toxic bacteria, and algae. One aspect of the invention is directed to a method and composition for treating water to sterilize the treated water of small and micro-sized aquatic pests including plants, animals, toxic bacteria, and microorganisms.

An object of the invention is to provide a method of treating water in a designated region of open water, an enclosed or a flow-restricted region to sterilize the area of aquatic pest microorganisms including plants, toxic bacteria, suspended animals, and other biologic organisms in sedimentary materials using at least one aquacidally active compound in an effective amount to be toxic to the target species.

A further object of the invention is to provide a method of treating ballast water in ships to control the transport of mollusks, dinoflagellates, toxic bacteria, algae and other microorganisms by treating the ballast water with an effective amount of an aquacidal compound to sterilize the ballast water.

Another object of the invention is to provide a method of treating water at an intake pipe of a process water system to sterilize the water of plants, animals and microorganisms.

A further object of the invention is to provide a method of treating ballast water to kill aquatic organisms found therein and to control their spread.

Still another object of the invention is to provide a method of treating a volume of water in an enclosed space or localized region of open water with a toxic amount of an aquacidal compound which is readily degraded to nontoxic by-products.

Another object of the invention to provide a method of inhibiting the spread of aquatic pests such as adult zebra mussels, zebra mussel larvae, oyster larvae, algal phytoplankton *Isochrysis galbana*, Neochloris, chlorella, toxic dinoflagellates (e.g. Prorocentrum), marine and freshwater protozoans and toxic bacteria (including vegetative cultures and encysted forms thereof), adult and larval copepods (vectors of *Vibrio Cholera* and *Vibrio fischeri*) and other planktonic crustaceans, e.g., *Artemia salina*, fish larvae and eggs by treating the water with an amount of at least one aquacidal compound of the type described herein in a quantity and for a sufficient period of time to kill the target aquatic pests.

A further object of the invention is to provide aquacidal compounds for the treatment of ballast water and water in other enclosed spaces, as biocidal additives to marine paints, and as agrochemicals for applying to plants for controlling snails and slugs.

Still another object of the invention is to provide a method of treating waste water from industrial and municipal sources to kill or control the spread of aquatic pest plant, animal and microorganisms.

These and other objects of the invention that will become apparent from the description herein are attained by method of inhibiting the growth of and preferably killing a population of a target pest microorganism by exposing said population to an effective amount of at least one aquacidal compound selected from the group consisting of: (a) quinones, (b) anthraquinones, (c) quinine, (d) warfarin, (e) coumarins, (f) amphotalide, (g) cyclohexadiene-1,4-dione, (h) phenidione, (i) pirdone, (j) sodium rhodizonate, (j) apirulosin, (k) thymoquinone, and (l) naphthalenediones which have the chemical structure of:

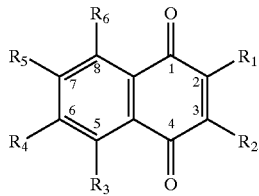

wherein:

$R_1$ is hydrogen, hydroxy or methyl group;

$R_2$ is hydrogen, methyl, sodium bisulfate, chloro, acetonyl, 3-methyl-2-butenyl, hydroxy, or 2-oxypropyl group;

$R_3$ is hydrogen, methyl, chloro, methoxy, or 3-methyl-2-butenyl group;

$R_4$ is hydrogen or methoxy group;

$R_5$ is hydrogen, hydroxy or methyl group;

$R_6$ is hydrogen or hydroxy group.

The aquacidal compounds according to the present invention are surprisingly effective in controlling populations of aquatic pest organisms at very low concentrations. Typical target aquatic pests small and microorganisms that are translocated by movement of the surrounding water, e.g., currents, tides, and intake ports. When the aquacides of the invention allowed to remain in contact with the target pest organisms for a period within the range of several hours to several days, the target pest population is killed. The aquacidal compounds are then degraded through the effects of ultraviolet light, oxidation, hydrolysis, and other natural mechanisms into benign by-products that allow the treated water to be returned to beneficial use.

DETAILED DESCRIPTION OF THE INVENTION

The present invention is generally directed to a method of treating water that hosts a target population of aquatic pests with an aquacidal agent for a sufficient period of exposure to reduce the target population in the treated water to benign levels or sterilize the treated water of the target population. The treated water can be located in a localized open water region, enclosed space or in a restricted flow path. Exemplary bodies of water that can be treated according to the invention include ship ballast water reservoirs, commercial process water taken in from a static or dynamic body of water, water ready to be discharged into a holding reservoir or waterway, cooling or other forms of holding ponds, intakes ports or pipes, discharge ports or pipes, heat exchangers, sewage treatment systems, food and beverage processing plants, pulp and paper mills, power plant intake and outlet pipes, cooling canals, water softening plants, sewage effluent, evaporative condensers, air wash water, canary and food processing water, brewery pasteurizing water, and the like. It is envisioned that the aquacidal agents of the present invention can also be used to treat shore areas or swimming regions if an aquatic pest population has reduced the recreational value of a region of water in a localized or localizable area in an otherwise open body of water.

In its preferred embodiments, the aquacidal agent made of one or more aquacidal compounds is added to ship ballast water at a concentration and for a period of exposure to the aquacidal compound that is effective in sterilizing the ballast water of target pests microorganisms. Such concentrations are typically sufficiently low to become diluted to a non-toxic level when discharged to a larger body of water so as to avoid or minimize harm to the indigenous species of plants and animals. Such a treatment method should help to prevent unintended migration of pest microorganisms between and among ports without significant capital expense or significant changes in commercial shipping practice.

The aquacidal compounds of the invention are mixed into the water using standard dispensing devices and dispensing methods as known in the art. The aquacidal compound can be dispensed as a single dose or over a period of time to maintain a desired concentration. Preferably, the aquacidal compound is introduced at a turbulent zone or other area where agitation will mix the aquacidal compound throughout the water to be treated. The aquacidal compound can be fed intermittently, continuously, or in one batch.

Target Pest Populations

Aquatic pest organisms and populations that can be controlled, killed, or otherwise rendered benign by the method of the invention are generally not free ranging between geographical regions of their own efforts but are subject primarily to the movement of the water currents or sediment around them. Such microorganisms move primarily under the influence of currents, tides, and ballast water taken in at one port and discharged at another. Aquatic pest microorganisms and populations that are targets for treatment according to the present invention include bacteria, viruses, protists, fungi, molds, aquatic pest plants, aquatic pest animals, parasites, pathogens, and symbionts of any of these organisms. A more specific list of aquatic pest organisms that can be treated according to the invention include, but are not limited to the following categories (which may overlap in some instances):

1) Holoplanktonic organisms such as phytoplankton (diatoms, dinoflagellates, blue-green algae, nanoplankton, and picoplankton) and zooplankton (jellyfish, comb jellies, hydrozoan, polychaete worms, rotifers, planktonic gastropods, snails, copedods, isopods, mysids, krill, arrow worms, and pelagic tunicates), and fish.

2) Meroplanktonic Organisms such as Phytoplankton (propagules of benthic plants) and Zooplankton (larvae of benthic invertebrates such as sponges, sea anemones, corals, mollusks, mussels, clams, oysters, and scallops).

3) Demersal organisms such as small crustaceans.

4) Tychoplanktonic organisms such as flatworms, polychaetes, insect larvae, mites and nematodes.

5) Benthic organisms such as leaches, insect larvae and adults.

6) Floating, Detached Biota such as sea grass, sea weed, and marsh plants.

7) Fish and shellfish diseases, pathogens, and parasites.

8) *Bythotrephes cederstroemi* (spiny water flea, spiny tailed water flea).

9) Macroinvertebrates, such as mollusks, crustaceans, sponges, annelids, bryozoans and tunicates. Examples of mollusks that can be effectively controlled are mussels, such as zebra mussels, clams, including asiatic clams, oysters and snails.

In further embodiments, the animals being treated are selected from the group consisting of bacteria, e.g., Vibrio spp. (*V. Cholera* and *V. Fischeri*), Cyanobacteria (blue-green algae), protozoans, e.g. Crytosporidiurn, Giardia, Naeglaria, algae, e.g., Pyrrophyta (dinoflagellates, e.g. Gymnodinium, Alexandrium, Pfiesteria, Gonyaulax Glenodinium (including encysted forms)), Cryptophyta, Chrysophyta, Porifera (sponges), Platyhelminthes (flat-worms, e.g., Trematoda, Cestoda, Turbellaria), Pseudocoelomates (e.g., Rotifers, Nematodes), Annelid worms (e.g., polychaetes, oligochates), Mollusks (e.g., Gastropods, such as polmonate snails), Bivalves, e.g., Crassostrea (oysters), Mytilus (blue mussels), Dreissena (zebra mussels), Crustaceans, larval-adult forms of copepods, ostracods, mysids, gammarids, larval forms of decapods, and Larval teleost fish.

The method of the invention in a first embodiment adds an effective amount of at least one marine plant and animal growth inhibiting compound to the water to be treated. The aquacidal compound is selected from the group consisting of a quinone, naphthalenedione, anthraquinone, and mixtures thereof. The quinones have the formula:

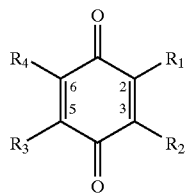

where $R_1$ is hydrogen, methyl, hydroxy or methoxy group;

$R_2$ is hydrogen, hydroxy, methyl, methoxy or —$NO_2$ group;

$R_3$ is hydrogen, hydroxy, methyl or methoxy group; and $R_4$ is hydrogen, methyl, methoxy, hydroxy, or —$NO_2$ group.

Examples of quinones found to be effective in controlling or inhibiting plant and animal growth in water include 1,4,benzoquinone (quinone), 2,5-dihydroxy 3,6-dinitro-p-benzoquinone (nitranilic acid), 2,6-dimethoxybenzoquinone, 3-hydroxy-2-methoxy-5-methyl-p-benzoquinone (fumagatin), 2-methylbenzoquinone (toluquinone), tetrahydroxy-p-benzoquinone (tetraquinone), 2,3-methoxy-5-methyl-1,4-benzoquinone, 2,3-methoxy-5-methyl-1,4-benzoquinone, and mixtures thereof. In further embodiments, the quinone can be an ubiquinone having the formula

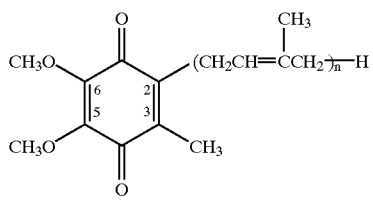

where n is an integer from 1 to 12. A particularly preferred ubiquinone has the formula above where n=10. In further embodiments, the ubiquinone has the above formula where n=6 to 10 and n is an integer.

In the embodiments where the marine plant and animal inhibiting composition is a naphthalenedione other than juglone, such naphthalenediones having the formula:

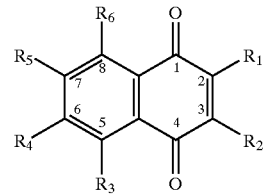

wherein $R_1$ is hydrogen, hydroxy or methyl group;

$R_2$ is hydrogen, methyl, sodium bisulfate, chloro, acetonyl, 3-methyl-2-butenyl or 2-oxypropyl group;

$R_3$ is hydrogen, methyl, chloro, methoxy, or 3-methyl-2-butenyl group;

$R_4$ is hydrogen or methoxy group;

$R_5$ is hydrogen, hydroxy or methyl group;

$R_6$ is hydrogen or hydroxy group.

Examples of naphthalenediones include 1,4-naphthalenedione, 2-methyl-5-hydroxy-1,4-naphthalenedione (plumbagin), 2-methyl-1,4-naphthalenedione (Vitamin $K_3$), 2-methyl-2 sodium metabisulfite-1,4-naphthalenedione, 6,8-dihydroxy benzoquinone, 2,7-dimethyl-1-4-naphthalenedione (chimaphilia), 2,3-dichloro-1,4-naphthalenedione (dichlorine), 3-acetonyl-5,8-dihydroxy-6-methoxy-1,4-naphthalenedione (javanicin), 2-hydroxy-3-(3-methyl-2-butenyl)-1,4-naphthalenedione (lapachol), pirdone, and 2-hydroxy-3-methyl-1,4-naphthalenedione (phthiocol).

The anthraquinones have the formula:

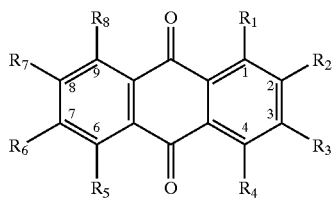

wherein $R_1$ is hydrogen, hydroxy or chloro;

$R_2$ is hydrogen, methyl, chloro, hydroxy, carbonyl, or carboxyl group;

$R_3$ is hydrogen or methyl group;

$R_4$ is hydrogen;

$R_5$ is hydrogen or hydroxyl group;

$R_6$ and $R_7$ are hydrogen; and $R_8$ is hydrogen or hydroxyl group.

Examples of anthraquinones that are suitable for treating water to control or inhibit marine plant and animal growth include 9,10 anthraquinone, 1,2-dihydroxyanthraquinone (alizarin), 3-methyl-1,8-dihydroxyanthraquinone, anthraquinone-2-carboxylic acid, 1-chloroanthraquinone, 2-methyl-anthraquinone, and 1-5 dihydroxyanthraquinone, 2-chloroanthraquinone.

Other compounds that can be used to control plant, animal, and microorganism growth either alone or in combination with each other and the quinones, naphthalenediones, and anthraquinones noted above include 9,10-dihydro-9-oxoanthracene (anthrone), 6'-methoxycinchonan-9-ol (quinine), 4-hydroxy-3-(3-oxo-1-phenyl butyl) -2H-1-benzopyran-2-one (warfarin), 2H-1- benzopyran-2-one (coumarin), 7-hydroxy-4-methylcoumarin, 4-hydroxy-6-methylcoumarin, 2[5-(4-aminophenoxy)pentyl]-1isoindole 1,3-(2H)-dione (amphotalide), sodium rhdixonate, 2-phenyl-1,3-indandione (phenindione), 2,5 dihydroxy-3-undecyl-2,5 cyclohexadiene, spirulosin and thymoquinone.

Compounds that are particularly effective in controlling macroinvertebrates include 2,3-methoxy-5-methyl-1,4-benzoquinone, 2-methyl-1,4-naphthalenedione, 2-methyl-5-hydroxy-1,4-naphthalenedione, 2-methyl -2-sodium metabisulfite-1,4-naphthalenedione, 3-methyl-1,8-dihydroxyanthraquinone, 2-methyl-anthraquinone, 1,2-dihydroxyanthraquinone, 1,4-naphthalenedione, and mixtures thereof. These compounds are also effective in controlling the growth of dinoflagellates.

In one embodiment of the invention, mollusks, dinoflagellates, toxic bacteria, and algae are treated to inhibit growth by applying an effective amount of compound selected from the group consisting of, 2,3-methoxy-5-methyl-1,4-benzoquinone, 2-methyl-1,4-naphthalenedione, and mixtures thereof.

One preferred embodiment of the invention is directed to a method of killing or inhibiting the growth of mollusks, dinoflagellates, toxic bacteria, and/or algae by exposing the mollusks, dinoflagellates, toxic bacteria, and/or algae to an effective amount of a quinone, anthraquinone, naphthalenedione, or mixture thereof. The method is effective in inhibiting the growth of toxic bacteria and mussels—particularly zebra mussels, and zebra mussel larvae, as well as other bivalves—by applying the aquacide compound to the water in an effective amount. In a preferred embodiment, mussels, and particularly zebra mussels and zebra mussel larvae, are treated to kill or inhibit their growth by exposing the zebra mussels to a toxic amount of a molluskocide compound selected from the group consisting of 2,3-methoxy-5-methyl-1,4-benzoquinone, 2-methyl-5-hydroxy-1,4-naphthalenedione, 2-methyl-1,4-naphthalenedione, 2-methyl-2-sodium metabisulfite-1,4-naphthalenedione, 3-methyl-1,8-dihydroxyanthraquinone, 2-methylanthraquinone, and mixtures thereof.

In a further embodiment, these aquacidal compounds are incorporated as an active compound into a solid or liquid bait for agricultural use to kill or inhibit the growth of snails and slugs. The bait can be a standard bait as known in the art. In other embodiments, the aquacidal compound is formed into a solution or dispersion and applied directly to the plant in an effective amount to treat the plant for controlling snails and slugs.

Aquacidal Amount

The amount of the aquacidal ingredient to be added will depend, in part, on the particular compound and the species of plant or animal being treated. As used herein, the term "effective amount" or "aquacidal" refers to an amount that is able to kill the target species or render the target specie population inert and otherwise not viable of sustained vitality.

The method for treating water to kill a target plant or animal introduces the aquacidal compound to the water in the amount of less than 1 wt %. Preferably, the aquacidal compound is added in an amount within the range of about 100 ppb to about 500 ppm (parts per million), more preferably in an amount within the range from about 500 ppb to about 300 ppm, most preferably within the range of 500 ppb to 250 ppm, and especially in an amount within the range of 1 ppm to about 250 ppm. Generally, the amount of the aquacidal compound used in treatment of ballast tank water will range from about 1 ppm to about 200 ppm.

The target pest population should be exposed to the aquacide at the selected concentration for a time sufficient to kill the target population. Exposure periods sufficient are generally within the range of a at least one hour to a period of less than 96 hours (4 days) for both fresh water as well as salt water. A preferred exposure is within the range from about two hours to about 48 hours. Routine sampling and testing can be used to determine precise concentrations and exposure durations for a specific aquacidal compound, water type, target population, method of introduction, and temperature.

Coatings

The aquacidal compounds of the invention can also be added to paints and coatings in a concentration sufficient to provide population control without adversely affecting the efficacy of the coating. The paint or coating composition can be applied to a surface, such as the hull of a boat, intake pipes, ship chests, anchors, and other underwater structures to prevent the plants and animals from growing and adhering to the surface.

The paint or coating composition can be conventional marine paint containing various polymers or polymer-forming components. Examples of suitable components including acrylic esters, such as ethyl acrylate and butyl acrylate, and methacrylic esters, such as methyl methacrylate and ethyl methacrylate. Other suitable components include 2-hydroxyethyl methacrylate and dimethylaminoethyl methacrylate that can be copolymerized with another vinyl monomer, such as styrene. The paint contains an effective amount of at least one aquacidal compound to inhibit plant an animal growth on a painted substrate. In embodiments of the invention, the aquacidal compound is included in an amount to provide a concentration of the aquacidal compound at the surface of the coating of at least 500 ppb, preferably about 1 ppm to 50 wt %, and more preferably within the range of 100–500 ppm to provide a plant and animal controlling amount of the aquacide compound in the coating.

EXAMPLES

The effectiveness and toxicity levels of the compounds were evaluated using active plant and animal species. The various compounds were added to the water at controlled rates and amounts. The results were observed and are recorded in Table 1 below.

The compounds were tested for efficacy on various plant and animal species according to the following protocols.

(a) Zebra Mussels (Larvae and Adults)

Zebra mussel broodstock were maintained in natural well water with calcium and magnesium adjusted to a hardness level equivalent to approximately 25 mg/l hardness.

At 20° C., larvae remain in the free-swimming state for 30–40 days prior to settlement. Bioassays using early larval stages of this species are variants on standard oyster embryo bioassays. Assays are conducted at the embryo, trochophore and D-hinge stage.

The assays examined the toxicity of various quinones to the earliest life history stages, namely embryo to trochophore stage (2–17 hours); trochophore stage (2–17 hours); trochophore to D-hinge stage (17–48 hours); and embryo to D-hinge stage (2–48 hours).

Approximately 25 adults from broodstock (held at 10–12° C.) were cleaned of debris and transferred to 1500 ml glass beakers containing approximately 800 ml of culture water. Water temperature was rapidly raised to 30–32° C. by the addition of warm water. Mussels treated this way usually spawn within 30 minutes. If no spawning occurred within this time, a slurry made from ripe gonads homogenized in culture water is added.

A successful spawn yielded >50,000 eggs/female. To check for successful fertilization, zygotes were transferred to a Sedgewick-Rafter cell for counting and examination under a binocular microscope. Fertilized eggs were seen to be actively dividing and reached the 8-cell stage between 2–3 hours following fertilization. A better than 70% fertilization rate is considered indicative of viable experimental material.

Assays were conducted on at least 500 embryos/larvae in each of 4 replicates. A range of 5 test concentrations (in the ppm range) plus controls were used. A density of 10 embryos per ml were used for embryo assays, and for D-hinge larvae 2 larvae/ml were used. The tests were static non-renewal. Any assay lasting 24 hours or longer received food (cultured Neochloris @ 5×104 cells ml-l) at 24 hour intervals.

Following counting and adjustment of densities, embryo assays were started as early as 2 hours following fertilization by inoculating a known number of embryos into the test media. Late stages were held in culture water until inoculation. Survivors were counted using Sedgewick-Rafter cells, with adjustments for control mortality using Abbott's formula. Probit and Dunnett's test are used to obtain the LD50, Lowest Observed Effect Concentration (LOEC) and No Observed Effect Concentration (NOEC) (Toxcalc 5.0).

(b) Fathead Minnow Acute Assay (Fish assay)

Fathead minnows (Pimephales promelas) from in-house laboratory cultures were used for these tests. Animals were cultured in natural well water with hardness adjusted to >50 ppm ($CaCO_3$) equivalents. Fish were spawned in a 20 gal spawning tank containing PVC tubing as refuges. Newly hatched larvae were transferred to a holding tank at densities of 50–100/1 until use. Brine shrimp nauplii (Artemia) were used as food.

The tests were static renewal. The test durations were 48 hours and 96 hours. The temperature was 20° C. ±1° C. Light quality was ambient laboratory illumination. Light intensity was 10–20 E/m$^2$/sec (50–100 ft-c). The photoperiod was 16 hours of light and 8 hours of dark. The test container was 400 ml. Renewal of test solutions occurred at 48 hours. The age of test organisms was 1–14 days, with a 24 hour age range. There were 10 organisms per container. There were 3 replicates per concentration of individual quinones in the ppm range. There are 5 test concentrations plus controls (initial range-finding tests performed on logarithmic series). All tests were conducted within 5 hours of dissolving the test compound. Animals were fed Artemia nauplii prior to the test and 2 hours prior to the 48 hour test solution renewal. Oxygen levels were maintained at >4.0 mg/L. Natural well water adjusted to >50 mg/L hardness equivalents was used for dilution.

The test objectives are to determine LC50,LOEC and NOEC. The test acceptability threshold is 90% or greater survival in controls. Data are analyzed using Toxcalc 5.0.

(c) Dinoflagellate (Prorocentrum Minimum) Assay

The dinoflagellate prorocentrum minimum was cultured at the Chesapeake Biological Laboratory culture facility from in-house stocks grown up as a 1 liter culture in sterilized 16 ppt salinity filtered water fortified with f/2 nutrient media. The culture was diluted to 5 liters with filtered estuarine water 16 ppt salinity prior to the experiments. The approximate starting cell density was 2×10$^6$ cells per ml.

Each 600 ml glass beaker containing 400 ml dinoflagellate culture was allowed to grow under continuous fluorescent light following the exposure treatments. At daily intervals, samples were taken for cell counting and microscopical examination, extraction of chlorophyll pigments with acetone and for direct in-vivo chlorophyll fluorescence determination.

100 ml of each dinoflagellate culture treatment in triplicate were filtered through a 25 mm GFF filter under gentle vacuum. The filters were folded and placed in polypropylene centrifuge tubes and exactly 4 ml of HPLC grade acetone added. The samples were sonicated with a probe (Virsonic 50) for approximately 2 minutes to disrupt cells after which they are allowed to extract at 4° C. overnight in a refrigerator. After centrifuging for 5 minutes, the supernatant was transferred to a quartz fluorometer cell and the fluorescence recorded using a Hitachi F4500 scanning fluorescence detector. Excitation was fixed at 436 nm with a 10 nm slit and the emission is recorded at 660 nm with a 10 nm slit. The photomultiplier is operated at 700 V. Authentic chlorophyll a and b (Sigman Chemicals) were dissolved in HPLC grade acetone to calibrate the spectrofluorometer. Three point calibrations were performed in triplicate on a daily basis and relative fluorescence response converted into units of ug/l.

In-vivo fluorimetry with the Hitachi F4500 involves suspending the algal cells and transferring an aliquot to a disposable polycarbonate cuvette and recording the emission spectra from 600–720 nm with excitation fixed at 436 nm with a 10 nm slit width.

Direct cell counts were made with a compound binocular microscope and a hemacytometer counting triplicate samples in 80 squares.

End-points for quinone toxicity include cell motility, inhibition of cell division, inhibition of chlorophyll synthesis and chloroplate bleaching.

(d) Chlorella Assay

Assays for other species of phytoplankton including Chlorella sp. and Isochrysis galbana followed the above outlined procedures.

(e) Copepod Assays (Eurytemora Affinis)

Cultures of Eurytemora affinis were continuously maintained in 15 seawater in a 8/16 hours light/dark regime fed every 48 hours on Isochrysis galbana. Toxicity bioassays are conducted on early instar naupliar larvae (chronic mortality/ fecundity assay) or adults (acute LC50 assay).

Larvae were collected as follows. Cultures were filtered with a 200 m Nitex filter to separate the adults from earlier stages. Adults were then allowed to spawn for 48–72 hours in order to produce stage 1–3 naupliar larvae to be used for the assay. Assays were conducted on batches of 10 larvae per treatment (in triplicate). At 20° C., assays were continued for 12 days (shorter at higher temperatures). Endpoints were the percentage of F0 generation (present as adults) and total numbers of F1 generation (present as eggs or naupliar larvae). LC50 assays on adult copepods were conducted for 24 or 48 hours with percentage mortality as the end-point. All assays were conducted at 15 salinity on a 8 hour/16 hour light/dark regime.

(f) Dinoflagellate Cysts (Glenodinium sp.)

Dinoflagellate cysts were collected from marine sediments cleaned of debris using mild ultrasonic cleansing and exposed to ppm levels of variety of quinones. Light microscopy and epifluorescence microscopy were employed to examine the cysts for oxidative damage and chloroplast disruption following treatment at the ppm level.

TABLE 1

| Ex. | IUPAC Nomenclature | Empirical Formula | Organism | Toxicity Data |
|---|---|---|---|---|
| (1) | 2-methyl-5-hydroxy-1,4-napthoquinone | $C_{11}H_8O_3$ | T. isochrysis galbana | Toxic at 50 ppb |
| | | | Neochloris | Toxic at 500 ppm |
| | | | Zebra larvae | Toxic at 200 ppb |
| | | | E. affinis | 5 ppm < 10 min |
| | | | Artemia salina | Toxic at 5 ppm |
| | | | Fish eggs | Kills & hatch prevention @ 1 ppm |
| | | | Minnow larvae | Toxic at 1 ppm |
| (2) | 2-methyl-1,4-naphthalenedione (Vitamin $K_3$) | $C_{11}H_8O_2$ | T. isochrysis galbana | Toxic at 500 ppb |
| | | | Zebra mussel larvae | Toxic at 500 ppm |
| | | | Oyster larvae | 1 ppm |
| | | | E. affinis | 5 ppm < 15 min |
| | | | Artemia salina | Toxic at 5 ppm |
| | | | Fish eggs | Kills & hatch prevention @ 1 ppm |
| (3) | 2-methyl-2-sodium metabisulfite-1,4-naphthalenedione | $C_{11}H_{10}SO_5Na$ | T. isochrysis galbana | Toxic at 500 ppb |
| | | | Zebra larvae | Toxic at 1 ppm |
| | | | Oyster larvae | 500 ppb |
| | | | E. affinis | 5 ppm < 15 min |
| | | | Artemia salina | Toxic at 5 ppm |
| | | | Fish eggs | Kills & hatch prevention @ 1 ppm |
| (4) | Anthrone | $C_{14}H_{10}O$ | T. isochrysis galbana | Toxic at 2 ppm |
| (5) | 1,2-dihydroxyanthraquinone | $C_{14}H_8O_4$ | T. isochrysis galbana | Toxic at 1 ppm |
| | | | E. affinis | Toxic at 1 ppm |
| | | | Artemia salina | Toxic at 5 ppm |
| (6) | 3-methyl-1,8-dihydroxyanthraquinone | $C_{15}H_{10}O_4$ | T. isochrysis galbana | Toxic at 1 ppm |
| | | | Zebra mussel larvae | Toxic at 1 ppm |
| (7) | anthraquinone-2-carboxylic acid | $C_{15}H_8O_4$ | T. isochrysis galbana | Toxic at 1 ppm |
| | | | E. affinis | 5 ppm < 5 hours |
| (8) | 1-chloroanthraquinone | $C_{14}H_7O_2$ | T. isochrysis galbana | Toxic at 500 ppb |
| | | | Neochloris | Toxic at 500 ppb |
| | | | E. affinis | 5 ppm < 5 hours |
| (9) | 2-methylanthraquinone | $C_{15}H_{10}O_2$ | T. isochrysis galbana | Toxic at 500 ppb |
| | | | Neochloris | Toxic 1 ppm |
| | | | Zebra larvae | Toxic at 200 ppm |
| | | | E. affinis | 5 ppm < 45 min |
| | | | Artemia salina | Toxic at 5 ppm |
| (10) | 1,4-naphthalenedione | $C_{10}H_6O_2$ | T. isochrysis galbana | Toxic at 1 ppm |
| | | | Oyster larvae | Toxic at 5 ppm |
| | | | E. affinis | 5 ppm < 10 min |
| (11) | anthraquinone | $C_{14}H_8O_2$ | E. affinis | 5 ppm < 4 hours |
| (12) | 1,4-benzoquinone | $C_6H_4O_2$ | T. isochrysis galbana | Toxic at 500 ppb |
| | | | Fish eggs | 50% mortality at 5 ppm. Control hatch at 1 ppm |
| (13) | methyl-1,4-benzoquinone (toluquinone) | $C_7H_6O_2$ | T. isochrysis galbana | Toxic at 500 ppb |
| (14) | 2,3-methoxy-5-methyl-1,4-benzoquinone | $C_9H_{10}O_4$ | T. isochrysis galbana | Toxic at 5 ppm |

Example 15

Banana snails (Bulimulis alternata) were obtained from a commercial supplier and were fed lettuce leaves until the start of the bioassay.

Ten snails were placed in covered 1 liter glass beakers, on approximately 50 cm$^2$ lettuce leaves which had been sprayed with a fine mist of an aqueous solution of 2,3-methoxy-5-methyl-1,4-benzoquinone at three concentrations: 5, 10 and 20 mg/l. The treated leaves were allowed to dry before exposure to the snails. 10 snails were placed on approximately 50 cm$^2$ of untreated lettuce leaf as a control. Treatments and controls were maintained at approximately 20° C. in the dark. They were observed at 24 and 48 hours for signs of mortality and feeding activity.

In all treatments, the snails demonstrated significant avoidance relative to control. Several snails of the treatment group withdrew into their shells and exhibited no feeding activity at all (leaves were completely intact). Others climbed up the walls of the beakers away from the leaves. This avoidance behavior was again observed after 48 hours. In contrast, the control group of snails consumed more than 10% of the leaf surface area after 24 hours and continued to feed and had consumed about 20% of the leaf after 48 hours.

While various embodiments have been selected to illustrate the invention, it will be understood to those skilled in the art that various changes and modifications can be made to the process disclosed herein without departing from the spirit and scope of the invention as defined in the appended claims.

What is claimed is:

1. A method for controlling a population of target aquatic pest microorganisms by applying an aquacidal compound to water infected with said target aquatic pest microorganisms, wherein said aquacidal compound comprises at least one anthraquinone and is applied in an amount that is effective to kill the target aquatic pest population.

2. The method of claim 1, wherein said population of target aquatic pest microorganisms is selected from the group consisting of viruses, protists, fungi, molds, plants, holoplanktonic organisms, meroplanktonic organisms, demersal organisms, benthic organisms, detached or floating biota, bacteria whether or not encysted, protozoans, algae, pyrrophyta, cryptophyta, chrysophyta, porifera, platyhelminthes, pseudocoelomates, annelid worms, zebra mollusks, bivalves, larval forms of copepods, ostracods, mysids, gammarids, larval forms of decapods, and larval teleost fish.

3. The method of claim 1, wherein said population of target pest microorganisms is selected from the group consisting of viruses, protists, holoplanktonic organisms, and meroplanktonic organisms.

4. The method of claim 1 wherein said population of target pest microrganisms is selected from the group consisting of demersal organisms, benthic organisms, detached or floating biota, bacteria whether or not encysted, and protozoans.

5. The method of claim 1 wherein said population of target pest microrganisms is selected from the group consisting of algae, pyrrophyta, cryptophyta, chrysophyta, porifera, platyhelminthes, pseudocoelomates, annelid worms, zebra mussels, bivalves, larval forms of copepods, ostracods, mysids, gammarids, larval forms of decapods, and larval teleost fish.

6. The method of claim 1 wherein said population of target pest microrganisms is selected from the group consisting of spiny water flea and bacteria.

7. A method according to claim 1 wherein said target aquatic pest is selected from the group consisting of bacteria whether or not encysted, protozoans, algae, dinoflagellates, dinoflagellate cysts, zebra mussels, and zebra mussel larvae.

8. A method according to claim 1 wherein said target aquatic pest is selected from the group consisting of bacteria, algae, dinoflagellates, dinoflagellate cysts, zebra mussels, and zebra mussel larvae.

9. A method according to claim 1 wherein said target aquatic pest is a bacteria.

10. A method according to claim 1 wherein said bacteria is a Vibrio species.

11. A method according to claim 1 wherein said target aquatic pest is a zebra mussel or zebra mussel larvae.

12. A method according to claim 1 wherein said target aquatic pest is a demersal organism.

13. A method according to claim 1 wherein said target aquatic pest is a benthic organism.

14. A method according to claim 1 wherein said target microorganism is a dinoflagellate cyst.

15. The method of claim 1, wherein said aquacidal compound has the formula:

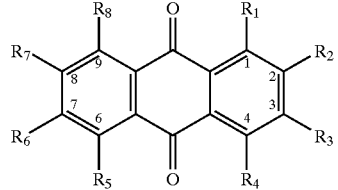

wherein $R_1$ is hydrogen, hydroxy, chloro;
$R_2$ is hydrogen, methyl, chloro, hydroxy, carbonyl, or carboxyl group;
$R_3$ is hydrogen or methyl group;
$R_4$ is hydrogen;
$R_5$ is hydrogen or hydroxyl group;
$R_6$ and $R_7$ are hydrogen; and
$R_8$ is hydrogen or hydroxyl group.

16. The method of claim 1, wherein said aquacidal compound is selected from the group consisting of 9,10 anthraquinone, 1,2-dihydroxyanthraquinone (alizarin), 3-methyl-1,8-dihydroxyanthraquinone, anthraquinone-2-carboxylic acid, 1-chloroanthraquinone, 2-methyl-anthraquinone, and 1-5 dihydroxyanthraquinone, 2-chloroanthraquinone.

17. The method of claim 1 wherein said aquacidal compound is present in an amount of less than 1 wt %.

18. The method of claim 1 wherein said aquacidal compound is present in an amount within the range of 100 ppb to 500 ppm.

19. The method of claim 1 wherein said aquacidal compound is present in an amount within the range of 500 ppb to 300 ppm.

20. The method of claim 1 wherein said aquacidal compound is present in an amount within the range of 1 ppm to 200 ppm.

21. The method of claim 1 wherein the target pest population is exposed to said aquacidal compound for at least one hour following application of said aquacidal compound.

22. The method of claim 21 wherein said target pest population is exposed to said aquacidal compound for 1–96 hours.

23. The method of claim 22 wherein said target pest population is exposed to said aquacidal compound for 2–48 hrs.

24. The method of claim 1 wherein said population of target pest microorganisms are located in a ballast water reservoir.

25. The method of claim 1 wherein said population is *Vibrio Cholera* or *Vibrio Fisheri*.

26. A method for killing a target population of mollusk pests in an aqueous system hosting said population comprising the step of:

adding to said aqueous system an amount of an aquacidal compound that is sufficient to kill said target population, said aquacidal compound having the formula:

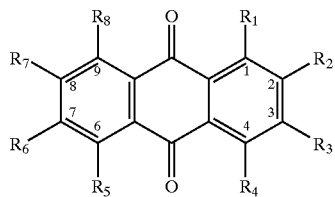

wherein $R_1$ is hydrogen, hydroxy, chloro;

$R_2$ is hydrogen, methyl, chloro, hydroxy, carbonyl, or carboxyl group;

$R_3$ is hydrogen or methyl group;

$R_4$ is hydrogen;

$R_5$ is hydrogen or hydroxyl group;

$R_6$ and $R_7$ are hydrogen; and $R_8$ is hydrogen or hydroxyl group.

27. The method of claim 26, wherein said mollusk pests are selected from the group consisting of mussels, clams and snails.

28. The method of claim 26, wherein said mollusk pests are selected from the group consisting of zebra mussels and Asiatic clams.

29. The method of claim 26 wherein said mollusk pests are exposed to said aquacidal compound for a period of time sufficient to kill said pests.

30. The method of claim 26 wherein said mollusk pests are exposed to said aquacidal compound for a period of time within the range of 1–96 hours and at a concentration within the range of 100 ppb to 500 ppm.

* * * * *